United States Patent
Wright

(12) 
(10) Patent No.: US 6,176,867 B1
(45) Date of Patent: Jan. 23, 2001

(54) MULTI-SIZE REUSABLE AORTIC PUNCH

(76) Inventor: John T. M. Wright, 555 S. Downing St., Denver, CO (US) 80220

( * ) Notice: Under 35 U.S.C. 154(b), the term of this patent shall be extended for 0 days.

(21) Appl. No.: 09/303,879

(22) Filed: May 3, 1999

(51) Int. Cl.[7] .................................................. A61B 17/32
(52) U.S. Cl. ............................................................. 606/184
(58) Field of Search ..................... 606/184, 167; 600/566, 567

(56) References Cited

U.S. PATENT DOCUMENTS

| | | | | |
|---|---|---|---|---|
| 3,949,747 | * | 4/1976 | Hevesy | 606/184 |
| 4,122,855 | * | 10/1978 | Tezel | 606/184 |
| 4,216,776 | * | 8/1980 | Downie et al. | 606/184 |
| 5,129,913 | * | 7/1992 | Ruppert | 606/184 |
| 5,910,153 | * | 6/1999 | Mayenberger | 606/184 |

\* cited by examiner

*Primary Examiner*—Michael H. Thaler

(57) ABSTRACT

Multi-size, reusable punches as sets for use in coronary artery bypass grafting that include punch/die assemblies that may easily and quickly interchanged at the operating table under sterile conditions and without tools are disclosed.

8 Claims, 1 Drawing Sheet

MULTI-SIZE REUSABLE AORTIC PUNCH

FIELD OF THE INVENTION

This invention relates to surgery generally and, more specifically to cardiovascular surgery and to instruments for attaching vessels to the aorta, and in analogous surgical procedures wherein on cannula-like vessel is attached to another cannula or to a tissue by a surgical procedure.

BACKGROUND OF THE INVENTION

This invention is an improvement over the aortic punches described and disclosed in the following U.S. Pat. No. 3,776,237, December 1973, Hill et al; U.S. Pat. No. 4,018, 228, April 1977, Goosen; and U.S. Pat No. 5,827,316, October 1998, Young et al.

Aortic punches are used in coronary artery bypass grafting when a section of saphenous vein graft is anastomosed to the aorta. Aortic punches have been in widespread clinical use for more than fifteen years.

Reusable aortic punches were initially used, however, they had at least two disadvantages. The first disadvantage was that several different sizes of instruments were necessary to provide adequate size range. The other main drawback was that some surgeons felt that there was uncertainty concerning how sharp the instrument was after a period of prolonged usage, and whether the instrument had become damaged during cleansing and handling since last used.

When disposable aortic punches were introduced, they soon found widespread favor, because they were readily available in a wide range of sizes, generally from about 2.5 mm to 6.5 mm diameters. Initially, the high cost of the single patient use device was not of major concern. However, with the ever spiraling cost of healthcare, clinical institutions seek ways to reduce costs.

This invention addresses the disadvantages of the early generation of reusable aortic punches and the high recurrent cost of the current disposable products.

It is an objective of this invention to provide a simple, reusable surgical tool for punching an aperture in the aorta for coronary artery bypass surgery using a saphenous vein graft.

It is a further objective of this invention to provide an aortic punch in which the punch and die portions may be easily and simply interchanged for a replacement set at the operating table under sterile conditions.

It is a further objective of this invention to provide an aortic punch in which the punch and die portions of a range of useful sizes may be easily and simply be fitted at the operating table under sterile conditions.

It is a further objective of this invention to provide an aortic punch in which the interchangeable punch and die portions have a surface treatment that aids in the retention of a sharp cutting edge, and reduced wear, galling and tissue adhesion.

It is an additional objective of this invention to provide an aortic punch in which the interchangeable punch and die portions when removed from the punch body have a sufficient restraining force so the punch will not fall out of the die under the influence of gravity.

Other objectives and advantages of this invention will be more apparent from the detailed description of the device which follows.

SUMMARY OF THE INVENTION

This invention relates to a reusable punch with interchangeable die and punch portions. Punches of the type described are most commonly used as aortic punches but, of course, they can be used whenever it is desired to punch a generally round hole through any thin walled tissue structure. The punch consists of a cylindrical tubular body with internal threads at either end, a cylindrical internal actuating rod member incorporating a "Tee" slot at one end and a threaded cross hole near the other, a die portion with an external thread at one end, a punch incorporating a retaining ring groove and a flange at one end and a disk shaped cutting flange at the other, a retaining ring, a finger actuating bar with a threaded central portion, a finger guard, a return spring and a thumb screw spring stop with an external threaded portion.

BRIEF DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENT

Figure 1:
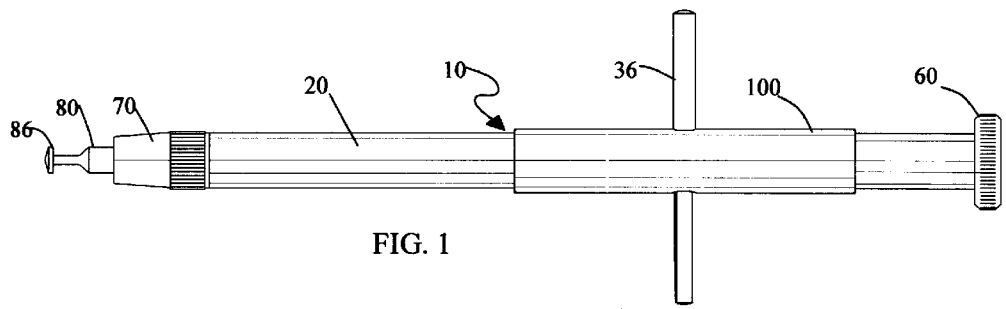
FIG. 1 shows a plan view of the aortic punch.

A presently preferred embodiment of the invention is depicted in the drawings and is described in detail hereinafter. Materials and dimensions, for example, will be discussed. It is to be clearly understood, however, that the invention is limited only be the claims and not by examples given in the following discussion. Materials can be varied, and absolute dimensions are not critical. It is, of course, important that dimensions of the components that work together in use be determined and the components constructed to perform the desired function and obtain the result sought after. Within these general limitations and guidelines, the invention can be varied and adapted as desired and necessary to provide suitable surgical instruments without departing from the invention.

Figure 2:
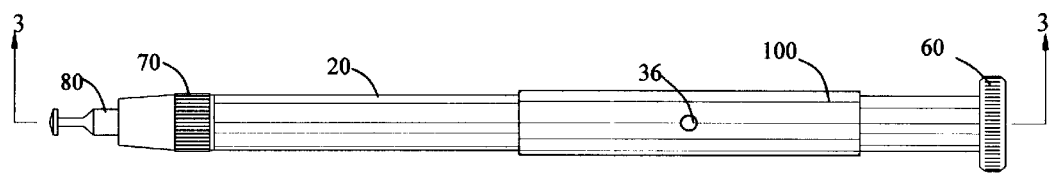
FIG. 2 shows a side view of the aortic punch.

The overall appearance and some limited functional information can be determined from FIGS. 1 and 2 to which reference is now made. The aortic punch 10 shown in FIGS. 1 and 2 comprises a main sleeve 20 to which an end cap 60 is attached at the distal end thereof and punch die 70 is attached at the proximal end. A punch 80 is slidably received in the die 70 and connected to be moved by the operating bar 36, which extends through an external slidable sleeve 100. The specific structure and function of the die and punch are the focus of the present invention and are described more fully below in connection with FIGS. 3 through 7. Briefly, however, punch tip 80 is inserted through an incision in the aorta and the operating bar 36 retracts the punch into the die to punch a hole through the aorta of a precise dimension.

Figure 3:
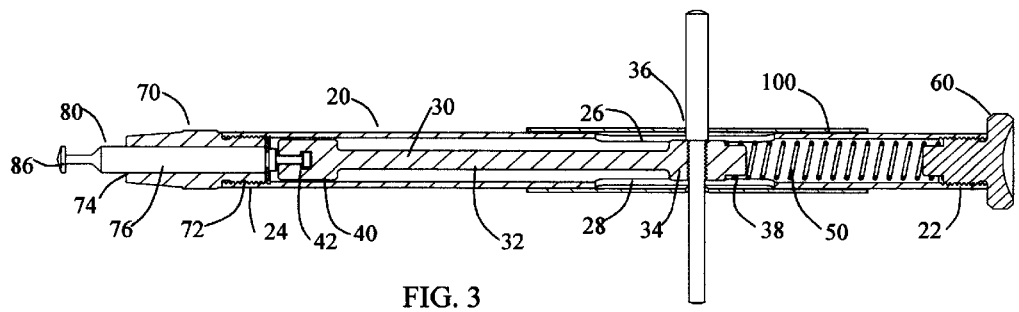
FIG. 3 shows a cross-sectional view of the aortic punch in the direction of arrows 3—3 of FIG. 2.

Referring now to FIG. 3, which is a cross-sectional view taken along line 3—3 of FIG. 2, The main cylinder 20 will be seen to be an elongate cylindrical tube constructed to define internal threaded receiving structures 22 at the distal end and 24 at the proximal end, having a pair of opposed slots 26 and 28 formed through the cylinder walls intermediate the ends.

Figure 7:
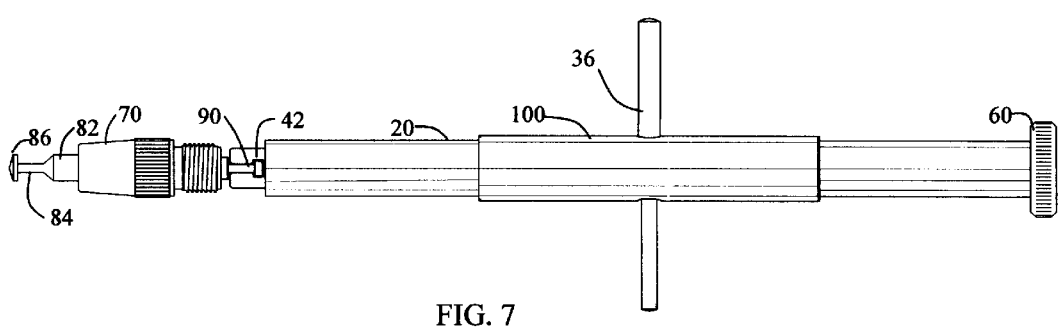
FIG. 7 shows a plan view of the aortic punch with the die unscrewed from the body in the interchangeable position.

An elongate actuator slide 30 is slidably received in the main cylinder 20. The actuator slide 30 may, except as specified hereinafter with respect to the proximal end portion, be of any suitable configuration to reciprocate freely in the cylinder 20. In the preferred embodiment, the actuator slide 30 is an elongate structure having a generally central axis, comprising a central shaft 32, a distal end portion through which a threaded passage is formed through which an operator bar 36 extends, being threadably secured in the threaded passage. The distal end portion may optionally define a spring seat 38. The slide 30 also comprises a proximal end portion 40 which has, extending from the distal end, a lateral Tee slot 42 defining a transverse passage. The Tee slot is formed all or part way in the end perpendicular to the axis of the slide, as shown in FIGS. 3 and 7. In the preferred embodiment, the Tee slot extends diametrically across the end having an opening of a first width at the end that intersects a transverse larger passage portion spaced from the end.

The actuator slide 30 is biased toward the proximal end in the main cylinder 20 by a spring 50 secured in the cylinder by a knurled thumb screw 60.

A punch die 70, having a distal threaded portion 72 is threadably received in the threaded proximal end 24 of the main cylinder 20. The punch die is so configured and constructed as to define a circular cutting die portion 74 on the proximal end and a passage 76 extending from end to end thereof.

Figure 4:
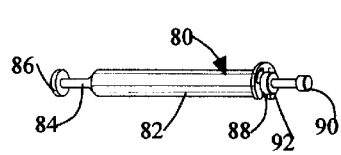
FIG. 4 shows an isometric view of a replaceable punch and with a retainer ring attached.

A knife member 80, best shown in FIGS. 3 and 4, in the form of an elongate cylinder is slidably received in the passage 76 of the die. The knife 80 is configured and constructed to define a guide portion 82 to guide the knife in accurate slidable relationship in the die passage 76 and a reduced diameter shaft portion 84 on the proximal end portion supporting a knife disc 86 which is at the end of the knife member. The knife member also defines, in the preferred embodiment, a keeper slot 88 proximate the distal end and a Tee-shaped bead 90 forming the distal end of the knife member. A keeper washer 92 is, in the preferred embodiment, fitted into the keeper slot for limiting the movement of the knife in the proximal direction in the die. Any keeper arrangement may, however, be used.

Figure 5:
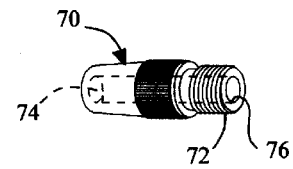
FIG. 5 shows an isometric view of a replaceable die.
Figure 6:
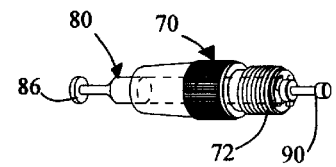
FIG. 6 shows an isometric view of a replaceable punch and die assembly.

Considering specifically FIGS. 4, 5 and 6, in connection with FIGS. 3 and 7, it will be seen that the knife member fits snugly into the passage 76 of the die and can be reciprocated therein.

Referring specifically to FIGS. 3 and 7, it will be seen that when the aortic punch is assembled, as shown in FIG. 3, the actuator slide 30 is releasably connected to the knife member 80 and that movement of the operator bar 36 toward the distal end of the main cylinder 20, to the night as shown in the drawings, retracts the knife 86 into position in the die end 74 thereby cutting a circular opening in any tissue through which the knife 86 may extend. In general, this mode of operation is disclosed in a very general sense in the aforementioned prior art patents, the disclosures of which are incorporated herein by reference.

Making very specific reference to FIG. 7, a very important structural and functional relationships in this invention are set forth.

When the die member 70 is unscrewed from the proximal end of the main cylinder, allowing the operator bar 36 to be moved toward the proximal end of the main cylinder 20, as shown in FIG. 7, it will be seen that the Tee-shaped head 90 can be slid laterally to remove it from the Tee slot 42 in the distal end of the actuator member 30, allowing removal of the die and cutter. The head 90 is described as Tee-shaped, which it is viewed from the side. In practice it is configured and constructed to define a shaft portion, which may be cylindrical but need not be, on which an enlarged head is formed, which may be cylindrical but need not be.

Now, if one had a series different sized die and knife assemblies, such as is shown in FIG. 5, in which the Tee-shaped head was the same size, and which had the same size distal threads 72, he or she could interchange these die and knife assemblies during surgery as needed for particular procedures. Thus, the need for a large number of expensive and space consuming assembled punches is obviated. This is exactly one of the important advantages provided by the present invention and not known or suggested in the prior art.

Thus, in one embodiment, the invention is contemplated to be a set comprising a holder, made up of all except the die and knife assembly, and a plurality of die and knife assemblies, such as, for example, shown in FIGS. 6 and 7 which are of different cutting sizes. For example, the invention would typically comprise one holder and a set of die and knife assemblies in which the knife and corresponding die diameters are, by way of example only, 3.0 mm, 3.6 mm, 4.0 mm, 4.4 mm, 4.8 mm, 5.2 mm, 5.6 mm and 6.4 mm in diameter.

It will be seen in FIGS. 3, 5 and 7, for example, that the knife 86 slides very snugly into the die passage 76 and that the die 74 is an annulus wherein the end extends substantially perpendicular to the axis of the die passage and the knife member. It has been considered in the past advantageous to define the die tip as, in effect, another blade, see, for example, Hill, et. al., U.S. Pat. No. 3,776,237. It has now been observed that the use of the double blade structure, exemplified by Hill's device, tend to result in a beveled cut through the aortic wall making the suture joint weaker and, sometimes, making suturing very difficult. The use of the flat perpendicular annulus die cuts passages through the aortic wall that have substantially cylindrical walls through the thickness of the tissue. This is another important facet of the invention.

It is important in the operating room that any device that must be or can be disassembled or assembled be so constructed as to permit the assembly and disassembly to be performed without requiring significant time and which eliminates or reduces the possibility of components falling into or near the operating field.

Thus, and an important feature of the present invention is providing knife-die combinations in which the knife and die are so magnetized that the knife member will not, of its own weight, fall out of the die. This maintains the proper assembly relationship and prevents separation of these components. The possibility of one of the components dropping into or near the operating field is greatly reduced.

Also, the knife member 80, or at least the distal end of it, and the actuator slide 30, or at least the proximal end thereof, may be magnetized to provide a magnetic field having a force sufficient to prevent the Tee-shaped head from falling from the Tee slot. This prevents the die-knife combination being removed from falling and retains the die-knife combination being installed until final assembly of the holder and die-knife combination.

The materials of which these components are made may be such as to be capable of being magnetized and retaining the magnetism after fabrication, or they may be made of magnetic materials, of which there are many. Alternatively, a magnetic component, e.g., a pin, may be inserted into or built into the components.

O-rings, ball detents and other keeper structures may, of course, be used in lieu of or in addition to the magnetic coupling, but magnetic coupling is a most convenient approach to the problem of maintaining relatively moveable parts in proper assemble.

Any of the many surgically acceptable materials may be used in manufacturing the aortic punch of this invention. Various stainless steels, cobalt alloys, and other iron or nickel containing alloys or titanium, for example, may be used. It is desirable, but not critical to the invention that the die and/or knife are manufactured from a hard metal alloy, e.g., in the range of about 40 to 60 Rockwell, or that the materials and/or coated so that the surface of the die and/or knife have a hardness generally in 80 to 90 Rockwell. The desired result is, at present, achieved by vapor deposition of a titanium nitride surface on the cutting surfaces of the knife and die. There are, of course, many methods and materials well-known in metallurgy that may be used to accomplish this result.

To summarize, the invention is embodied in an aortic punch in which the punch knife and die are re-useable and may be easily interchanged in the operating room. The invention provides a set which includes only one holder to which any of several sizes of knife-die assemblies, included in the set, can be attached quickly and easily to meet any need during a surgical procedure. There is, of course, great economy in using the present invention as compared with, for example, the reusable and disposable aortic punches of the prior art. The provision of a flat annulus perpendicular to the axis of the knife results in a more provision of a flat annulus perpendicular to the axis of the knife results in a more symmetrical hole through the aortic wall in which the walls of the hole are more cylindrical than has been accomplished in the past. The provision of magnetism in connection with the knife member and die, and optionally in connection with the actuator member provides a margin of safety in the operating room by reducing or preventing separation of the components of the invention.

The present invention is used in the same circumstances and, insofar as surgical procedures are concerned, in generally the same manner as the aortic punches disclosed in the aforesaid patents, namely: U.S. Pat. No. 3,776,237, December 1973, Hill et al, U.S. Pat. No. 4,018,228, April 1977, Goosen; and U.S. Pat. No. 5,827,316, October 1998, Young et al, the disclosure of which is referred to for further details. These surgical procedures and the use of aortic punches are well known and are the subject of surgical treatises and many journal publications; thus, the method of use is known to surgeons skilled in the relevant art.

INDUSTRIAL APPLICATION

This invention is useful in the medical instrument industry.

What is claimed is:

1. An aortic punch for surgical use in cutting a generally circular hole through the walls of the aorta or other tissue of a patient, comprising:

an elongate holder (10) having proximal and distal ends that comprises supporting structure (20), an actuator (30) supported by the supporting structure for reciprocal movement with respect thereto, and an operator (36) for moving the actuator reciprocally longitudinally of the supporting structure, the holder comprising means (24, 42) for supporting a die member and a knife member on the holder;

a die member (70) having proximal and distal ends, the die member defining a generally cylindrical passage (76) there through, means (72) on the distal end of the die member for being removably attached to the holder, and a cutting die (74) on the proximal end thereof; and a knife member (80) received in the passage in the die member for reciprocal movement, the knife member defining at the distal end thereof, means (90) at the distal end for removably attaching the knife member to the actuator in the holder, and a generally circular cutting knife (86) at the proximal end thereof;

the knife member or the die member comprising magnetic material producing a magnetic field sufficiently strong to retain the knife member in the die member.

2. The aortic punch of claim 1 wherein both the knife member and the die member comprise magnetic material.

3. An aortic punch set for surgical use in cutting a generally circular hole through the walls of the aorta or other tissue of a patient comprising:

an elongate holder (10) having proximal and distal ends that comprises supporting structure (20), an actuator (30) supported by the supporting structure for reciprocal movement with respect thereto, and an operator (36) for moving the actuator reciprocally longitudinally of the supporting structure, the holder comprising means (24, 42) for supporting a die member and a knife member on the holder;

a plurality of different sized die members (70), each of said die members having proximal and distal ends, the die member defining a generally cylindrical passage (76) there through, means (72) on the distal end of the die member for being removably attached to the holder, and a cutting die (74) on the proximal end thereof; and a plurality of different sized knife members (80) corresponding to the sizes of the die members, each of the respective knife members being receivable in the passage in the respective die members for reciprocal movement, the knife member defining at the distal end thereof, means (90) for removably attaching the knife member to the actuator in the holder and a generally circular cutting knife (86) at the proximal end thereof;

the knife members or the die members comprising magnetic material producing a magnetic field sufficiently strong to retain the knife member in the die member.

4. The aortic punch set of claim 3 wherein each of the respective knife members and the respective die members comprising magnetic material producing a magnetic field sufficiently strong to retain the respective knife members in the respective die members.

5. In an aortic punch for cutting a generally circular opening through the wall of the aorta or other vessel of a patient as part of a surgical procedure which comprises a generally circular die member and a generally circular knife member defining a generally circular knife slidably received in the die member and means for moving the knife into juxtaposition with the die for punching said opening, the improvement further comprising:

magnetic means for removably retaining the knife member in the die member such that the knife member cannot fall of its own weight from die member but can be removed by surgical personnel simply by pulling the knife member out of the knife member;

the knife member or the die member comprising magnetic material producing a magnetic field sufficiently strong to retain the knife member in the die member.

6. The aortic punch of claim 5 wherein both the knife member and the die member comprise magnetic material.

7. An aortic punch for surgical use in cutting a generally circular hole through the walls of the aorta or other tissue of a patient, comprising:

an elongate holder (10) having proximal and distal ends that comprises supporting structure (20), an actuator (30) supported by the supporting structure for reciprocal movement with respect thereto, and an operator (36) for moving the actuator reciprocally longitudinally of the supporting structure, the holder comprising means (24, 42) for supporting a die member and a knife member on the holder;

a die member (70) having proximal and distal ends, the die member defining a generally cylindrical passage (76) there through, means (72) on the distal end of the die member for being removably attached to the holder, and a case-hardened cutting die (74) on the proximal end thereof; and a knife member (80) received in the passage in the die member for reciprocal movement, the knife member defining at the distal end thereof, means (90) at the distal end for removably attaching the knife member to the actuator in the holder, and a case-hardened generally circular cutting knife (86) at the proximal end thereof;

the knife member or the die member comprising magnetic material producing a magnetic field sufficiently strong to retain the knife member in the die member.

8. The aortic punch of claim 7 wherein both the knife member and the die member comprise magnetic material.

* * * * *